(12) United States Patent
Boone et al.

(10) Patent No.: US 9,115,155 B1
(45) Date of Patent: Aug. 25, 2015

(54) LOW-PRESSURE SYNTHESIS OF CYCLOHEXANEDIMETHANOL AND DERIVATIVES

(71) Applicant: Eastman Chemical Company, Kingsport, TN (US)

(72) Inventors: Matthew Allen Boone, Gray, TN (US); Robert Thomas Hembre, Johnson City, TN (US)

(73) Assignee: EASTMAN CHEMICAL COMPANY, Kingsport, TN (US)

(*) Notice: Subject to any disclaimer, the term of this patent is extended or adjusted under 35 U.S.C. 154(b) by 35 days.

(21) Appl. No.: 14/220,264

(22) Filed: Mar. 20, 2014

(51) Int. Cl.
| | |
|---|---|
| *C07C 31/13* | (2006.01) |
| *C07C 51/16* | (2006.01) |
| *C07F 7/18* | (2006.01) |
| *C07C 29/46* | (2006.01) |
| *C07C 41/09* | (2006.01) |

(52) U.S. Cl.
CPC ............... *C07F 7/1896* (2013.01); *C07C 29/46* (2013.01); *C07C 41/09* (2013.01)

(58) Field of Classification Search
CPC ............................. C07C 2101/12; C07C 63/14
USPC ........................................... 568/831; 562/412
See application file for complete search history.

(56) References Cited

U.S. PATENT DOCUMENTS

| | | | |
|---|---|---|---|
| 1,891,043 A | 12/1932 | Diels et al. | |
| 1,944,731 A | 1/1934 | Diels et al. | |
| 2,349,232 A | 5/1944 | Joshel | |
| 3,081,334 A | 3/1963 | Kauer | |
| 3,334,149 A | 8/1967 | Akin et al. | |
| 3,903,188 A | 9/1975 | Citron | |
| 3,925,493 A | 12/1975 | Bader et al. | |
| 4,952,292 A | 8/1990 | Sridhar et al. | |
| 4,999,090 A | 3/1991 | Tateno et al. | |
| 5,387,752 A | 2/1995 | Scarlett et al. | |
| 5,387,753 A | 2/1995 | Scarlett et al. | |
| 5,395,986 A | 3/1995 | Scarlett et al. | |
| 5,395,987 A | 3/1995 | Rathmell et al. | |
| 5,395,990 A | 3/1995 | Scarlett | |
| 5,395,991 A | 3/1995 | Scarlett et al. | |
| 5,406,004 A | 4/1995 | Eastland et al. | |
| 5,414,159 A | 5/1995 | Appleton et al. | |
| 5,420,365 A | 5/1995 | Rittinger et al. | |
| 5,487,987 A | 1/1996 | Frost et al. | |
| 6,111,146 A | 8/2000 | Rayborn | |
| 6,187,968 B1 | 2/2001 | Itoh et al. | |
| 6,294,703 B1 | 9/2001 | Hara et al. | |
| 6,410,807 B1* | 6/2002 | Yang et al. | 568/831 |
| 6,410,809 B1 | 6/2002 | Kaneda et al. | |
| 6,632,331 B2 | 10/2003 | Yoshida et al. | |
| 6,919,489 B1 | 7/2005 | McCusker-Orth | |
| 7,385,081 B1 | 6/2008 | Gong | |
| 7,723,551 B2 | 5/2010 | McCusker et al. | |
| 8,273,926 B2 | 9/2012 | Bergman et al. | |
| 2010/0267997 A1 | 10/2010 | Miller et al. | |
| 2010/0314243 A1 | 12/2010 | Frost et al. | |
| 2011/0098514 A1 | 4/2011 | Miller et al. | |
| 2011/0282078 A1 | 11/2011 | Frost et al. | |
| 2011/0288263 A1 | 11/2011 | Frost et al. | |
| 2011/0288310 A1 | 11/2011 | Frost et al. | |
| 2011/0288311 A1 | 11/2011 | Frost et al. | |

FOREIGN PATENT DOCUMENTS

| | | |
|---|---|---|
| CA | 1215399 A | 12/1986 |
| EP | 1 114 810 A1 | 7/2001 |
| GB | 1015799 A | 3/1930 |
| WO | WO 2009/110402 A1 | 9/2009 |
| WO | WO 2010/151346 A1 | 12/2010 |
| WO | WO 2012/061272 A2 | 5/2012 |

OTHER PUBLICATIONS

Suzuki, Hideyuki, et al.; "Synthesis of eleven-membered carbocycles via a homo-Cope type of five-carbon ring expansion reaction utilized β-(hydroxymethyl)allylsilane"; Tetrahedron 59, pp. 3157-3174 (2003).

Achmatowicz, O., et al.; "The Application of Muconic Ester to Diene Additions", Bulletin De L'Academie Polonaise Des Sciences, Cl. III—vol. III, No. 10, (1995), pp. 557-564.

Bartlett, Paul D., et al.; "Cycloaddition. VIII. Ethylene as a Dienophile. A Minute Amount of 1,2 Cycloaddition of Ethylene to Butadiene", Journal of the American Chemical Society, 90:22, (1969), pp. 6071-6077.

(Continued)

*Primary Examiner* — Porfirio Nazario Gonzalez
*Assistant Examiner* — Kofi Adzamli
(74) *Attorney, Agent, or Firm* — Steven A Owen

(57) ABSTRACT

The invention is directed to a process for preparing a 1,4-disubstituted cyclohexane compound of formula (I):

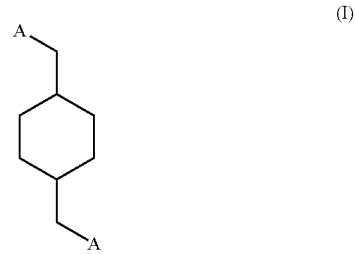

(I)

where A is —OH, —OR, Br, or Cl; and

R is a silyl group, a hydrocarbyl group, or an acyl group having 1 to 12 carbon atoms. The process includes the steps of reacting ethylene with a (2E,4E)-hexa-2,4-diene compound to produce a 3,6-disubstituted cyclohex-1-ene compound, and hydrogenating the 3,6-disubstituted cyclohex-1-ene compound to yield the 1,4-disubstituted cyclohexane compound of formula (I).

12 Claims, No Drawings

(56) References Cited

OTHER PUBLICATIONS

Carr, Richard V.C., et al.; "Dienophilic Properties of Phenyl Vinyl Sulfone and trans-1-(Phenylsulfonyl)-2-(trimethylsilyl)ethylene. Their Utilization as Synthons for Ethylene, 1-Alkenes, Acetylene, and Monosubstituted Alkynes in the Construction of Functionalized Six-Membered Rings via [4+2] π Cycloaddition Methodology"; J. Org. Chem., vol. 48, No. 25, (1983), pp. 4976-4986.

Kibler, Charles J., et al.; "Polyesters of 1,4-Cyclohexanedimethanol"; Journal of Polymer Science: Part A, vol. 2, pp. 2115-2125 (1964).

Williams, C. Luke, et al.; Cycloaddition of Biomass-Derived Furans for Catalytic Production of Renewable p-Xylene; ACS Catalysis, 2, pp. 935-939 (2012).

Chou, Grace F.; "Norbornene from Dicyclopentadiene and Ethylene", PEP Review 95-1-5. Jul. 1997.

Farmer, Ernest Harold, et al.; Properties of Conjugated Compounds. Part VII. The Additive Formation of cycloHexenes; Imperial College of Science and Technology, (1929) pp. 897-909.

Funel, Jacques-Alexis, et al.; "Industrial Applications of the Diels-Alder Reaction"; Angewandte Chemie International Edition, 52, (2013), pp. 3822-3863.

Shiramizu, Mike, et al.; "Deoxygenation of Biomass-Derived Feedstocks: Oxorhenium-Catalyzed Deoxydehydration of Sugars and Sugar Alcohols"; Angewandte Chemie International Edition, 51, (2012), pp. 8082-8086.

Reymond, Sebastien, et al.; "Copper-Catalyzed Diels-Alder Reacations"; Chemical Reviews, vol. 108, No. 12, (2008), pp. 5359-5406.

Joshel, Lloyd M., et al.; "The Synthesis of Condensed Ring Compounds. VII. The Successful Use of Ethylene in the Diels-Alder Reacation", Journal of American Chemical Society, vol. 63, (1941), pp. 3350-3351.

Chang, Sukbok, et al.; "Regio- and Enantioselective Catalytic Epoxidation of Conjugated Polyenes. Formal Synthesis of $LTA_4$ Methyl Ester"; The Journal of Organic Chemsity, vol. 58, No. 25, (1993) pp. 6939-6941.

Walsh, James G., et al.; "Easy access to medium rings by entropy/strain reduction. Part 2.[1] The ready availability of cis,cis-2,4-diene-1,6-diols and derived dibromides allows a simple and mild route to substituted 2,7-dihydro-1H-azepines" J. Chem. Soc., Perkin Trans. 1, (1999), pp. 3657-3665.

Smith, Michael, et al.; "The Diels-Alder Reaction"; March's Advanced Organic Chemistry, $5^{th}$ Edition, (2001), pp. 1062-1068.

Jursic, Branko, et al.; "DFT Study of the Diels-Alder reactions between ethylene with buta-1,3-diene and cyclopentadiene" Journal of the Chemical Society, Perkin Transactions 2, (1995), pp. 1223-1226 (Abstract).

Lemiegre, Loic, et al.; "Synthesis of α,β-unsaturated dioxanes, dioxolanes and dioxepanes by trans-acetalisation of dimethylacetals with meso or $C_2$-symmetrical 1,2-, 1,3- and 1,4-diols"; Tetrahedron 60, (2004), pp. 415-427.

Nudenberg, Walter et al.; "3,6-Epoxycyclohexene from Furan and Ethylene"; Journal of American Chemical Society, 66, (1944) pp. 307-308.

\* cited by examiner

LOW-PRESSURE SYNTHESIS OF CYCLOHEXANEDIMETHANOL AND DERIVATIVES

FIELD OF THE INVENTION

The invention generally relates to the preparation of cyclohexanedimethanol and its derivatives. More particularly, the preparation is based on the Diels-Alder cyclization of a 2,4-hexadiene compound with ethylene followed by the hydrogenation of the resulting cyclohexene compound.

BACKGROUND OF THE INVENTION

Currently, cyclohexanedimethanol (CHDM) is prepared industrially by a four-step process. The process involves (1) oxidizing p-xylene to terephthalic acid (TPA), (2) esterifying the TPA to produce dimethyl terephthalate (DMT), (3) hydrogenating the aromatic ring of DMT to yield dimethyl cyclohexanedicarboxylate (DMCD), and (4) hydrogenating the DMCD to obtain CHDM. The 1,4-CHDM produced is a trans-rich mixture of isomers (~60:40).

This four-step process suffers from a number of disadvantages. For example, all CHDM production depends on the capacity of the manufacturer to make DMT. DMT, however, has other valuable uses, including as a monomer to make terephthalate-based polyesters. Therefore, any diversion of DMT to make CHDM takes away from the supply that could go towards making other valuable products.

Another disadvantage of the current process for making CHDM is that it requires high-pressure hydrogenation (>4,000 psi) to reduce the two methyl-ester groups of DMT to the two hydroxy-methyl groups of CHDM.

Thus, there is a need in the art for a new route to making CHDM and its derivatives, particularly, one that does not require high-pressure hydrogenation.

The present invention addresses this need as well as others, which will become apparent from the following description and the appended claims.

SUMMARY OF THE INVENTION

The invention is as set forth in the appended claims.

Briefly, it has been surprisingly discovered that 2,4-hexadiene-1,6-diol (where R=H in the equation below) undergoes a Diels-Alder reaction with ethylene to yield a 3,6-dihydroxymethylcyclohexene, which upon hydrogenation at relatively low pressure (e.g., ~100 psi) produces CHDM.

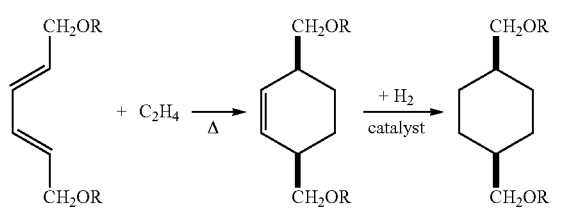

Derivatives of 2,4-hexadiene-1,6-diol, such as the bis-acetate ester or bis-silyl ether, also react via [4+2] cycloaddition with ethylene to produce 3,6-dimethylcyclohex-1-ene derivatives, which are similarly hydrogenated at low pressure to cyclohexane derivatives and may be subsequently deprotected by hydrolysis to yield CHDM.

If the hexadiene reacted in the Diels-Alder reaction is the trans,trans-isomer, then the cyclohexene derivative produced has its 1,6-substituents in a cis geometry. Thus, if the hydrogenation of the cyclohexene is carried out without isomerization, the CHDM produced is cis-CHDM. If isomerization of the cycloalkene occurs prior to, or faster than, its hydrogenation, then a mixture of cis- and trans-CHDM isomers results.

Thus, in one aspect, the present invention provides a process for preparing a 1,4-disubstituted cyclohexane compound of formula (I):

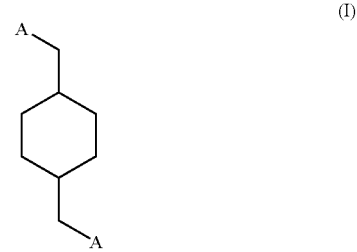

where A is —OH, —OR, Br, or Cl; and

R is a silyl group, a hydrocarbyl group, or an acyl group having 1 to 12 carbon atoms. The process comprises:

(a) contacting ethylene with a (2E,4E)-hexa-2,4-diene compound of formula (II):

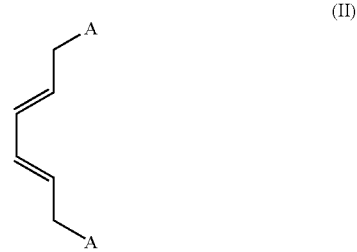

at conditions effective to produce a 3,6-disubstituted cyclohex-1-ene compound of formula (III):

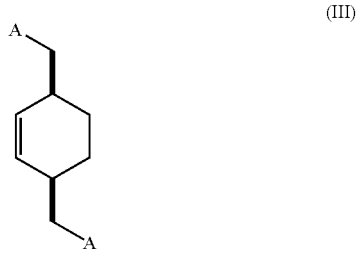

where A is as defined above; and (b) contacting the 3,6-disubstituted cyclohex-1-ene compound of formula (III) with hydrogen at conditions effective to produce the 1,4-disubstituted cyclohexane compound of formula (I).

DETAILED DESCRIPTION OF THE INVENTION

The present invention provides a process for preparing a 1,4-disubstituted cyclohexane compound of formula (I):

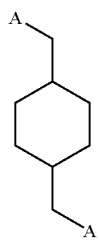

(I)

where A is —OH, —OR, Br, or Cl; and

R is a silyl group, a hydrocarbyl group, or an acyl group having 1 to 12 carbon atoms.

The silyl group may be represented by formula $SiR^1_3$ where each $R^1$ may be independently selected from a straight-chain or branched $C_1$ to $C_6$ alkyl group or an aryl group, such as methyl, ethyl, propyl, isopropyl, butyl, t-butyl, phenyl, and mixtures thereof. Examples of suitable silyl groups include trimethylsilyl: t-butyldimethylsilyl, and phenyldimethylsilyl.

The hydrocarbyl group can have 1 to 12 carbon atoms and may be substituted or unsubstituted, saturated or unsaturated, straight-chain or branched, or cyclic. For example, the hydrocarbyl group may be alkyl, aryl, cycloalkyl, alkaryl, or aralkyl. The hydrocarbyl group may be substituted with an ether group or a carbonyl group such as a ketone, ester or amide. Examples of hydrocarbyl groups include methyl, ethyl, propyl, isopropyl, butyl, isobutyl, sec-butyl, tert-butyl, pentyl, hexyl, heptyl, cyclohexyl, benzyl, phenyl, and β-methoxyethyl.

The acyl group has 1 to 12 carbon atoms. Examples of suitable acyl groups include acetyl, propionyl, butyryl, isobutyryl, benzoyl, and cyclohexylcarbonyl.

Examples of compounds of the formula (I) that can be made according the process of the present invention include 1,4-cyclohexanedimethanol, 1,4-cyclohexanedimethanol diacetate, 1,4-bis(chloromethyl)cyclohexane, 1,4-bis(bromomethyl)cyclohexane, 1,4-bis(((trimethylsilyl)oxy)methyl)cyclohexane, and 1,4-bis(((tert-butyldimethylsilyl)oxy)methyl)cyclohexane, and 1,4-bis(benzyloxymethyl)cyclohexane.

The first step in the process according to the invention involves contacting ethylene with a (2E,4E)-hexa-2,4-diene compound of the formula (II) at conditions effective to produce a corresponding 3,6-disubstituted cyclohex-1-ene compound of the formula (III).

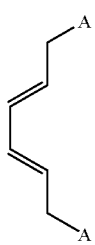

(II)

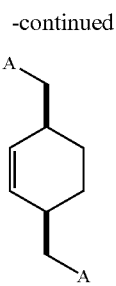

(III)

The "A" in formulas (II) and (III) is as defined in formula (I).

The starting hexadiene compounds of formula (II) may be obtained by several known methods from various starting materials. For example, dimethyl muconate can be converted to 2,4-hexadiene-1,6-diol by treatment with aluminum hydride reagents (Walsh et al., *J. Chem. Soc.*, Perkin Trans I, pp. 3657-65 (1999)), and muconic acid may be derived from glucose (Frost et al., U.S. Pat. No. 5,487,987 (Purdue Research Found., 1996)). Selective catalytic hydrogenation of muconates can make this an attractive synthesis of 2,4-hexadiene-1,6-diols from renewable materials.

Likewise, the 2,4-hexadiene-1,6-diol diacetates may be derived from a hexose such as sorbitol. With protection of the primary alcohol groups as acetates, rhenium-catalyzed dideoxydehydration (see Shiramizu et al., *Angew. Chem. Intl Ed.*, Vol. 51, pp. 8082-8086 (2012); and Bergman et al., U.S. Pat. No. 8,273,926 (Univ. of Cal., 2012)) can yield 2,4-hexadiene-1,6-diol diacetate.

2,4-Hexadiene-1,6-diol can also be readily produced by the oxidative coupling of two molecules of propargyl alcohol, yielding 2,4-hexadiyne-1,6-diol (Sridhar et al., U.S. Pat. No. 4,952,292 (Huels, 1990)), followed by hydrogenation of the di-yne (see *Handbook of Heterogeneous Catalytic Hydrogenation for Organic Synthesis*, Nishimura, 2001) and isomerization of Z,Z- to E,E-dienes (Citron, U.S. Pat. No. 3,903,188 (DuPont, 1975)).

Another acetylene-derived approach to this skeleton is reported in U.S. Pat. No. 5,420,365 (BASF, 1995) in which the diacetylide dianion is treated with formaldehyde. Likewise, Chang et al. describe a three-step synthesis beginning with 2-butyne-1,4-diol (*J. Org. Chem.*, Vol. 58, pp. 6939-6941 (1993)).

A 1,5-hexadiene-3,4-diol skeleton can be obtained by the reductive dimerization of acrolein (Smith, GB 1,015,799 (Shell, 1966)). Treating this with hydrochloric or hydrobromic acids yields the desired 2,4-hexadiene-1,6-disubstituted derivatives in good yield (Bader et al., U.S. Pat. No. 3,925,493 (Produits Chimiques Ugine Kuhlmann, 1975)).

The above methods are not meant to be exhaustive, but rather are merely illustrative of the possible routes to obtaining the starting hexadiene compounds of formula (II) from diverse starting materials. Other routes to 2,4-hexadiene-1,6-diol and its derivatives are also possible.

The conditions effective for reacting ethylene with the hexadiene compound (II) include a temperature of 140 to 300° C. and a pressure of 500 to 2,500 psig of ethylene. Other effective conditions include a temperature of 160 to 250° C. and a pressure of 1,000 to 2,000 psig of ethylene.

The reaction time may be varied, depending on the reaction conditions chosen and the desired yield. Generally, the Diels-Alder reaction time may vary, such as from 5 minutes to 3 hours, or from 10 minutes to 2 hours.

The Diels-Alder reaction for making the 3,6-disubstituted cyclohex-1-ene compound of formula (III) may be carried out in the presence, or in the absence, of a solvent. The solvent should be in the liquid state under reaction conditions. Examples of suitable solvents include water, aqueous salt solutions, and organic solvents. The aqueous salt solutions typically contain an alkali metal halide, such as LiCl. Typical organic solvents include hydrocarbons, acyclic ethers, alkyl polyethers, cyclic ethers, esters, alcohols, amides and chlorinated hydrocarbons. Examples of such organic solvents include xylene, decaline, toluene, hexane, tetrahydrofuran, glyme, diglyme, ethyl acetate, isopropyl acetate, dimethyl formamide, methylene chloride, dichrorobenzene, and the like.

Where a solvent is used, the concentration of the hexadiene compound (II) in the solvent may range from 0.2 to 4 molar (M), or from 0.5 to 3 M.

The Diels-Alder reaction may be carried out in the presence of a catalyst as described, for example, by Reymond et al., *Chem. Rev.*, Vol. 108, pp. 5359-5406 (2008) and Funel et al., *Angew. Chem. Intl. Ed.*, Vol. 52, pp. 3822-63 (2013).

The second step in the process according to the invention involves contacting the 3,6-disubstituted cyclohex-1-ene compound (III) with hydrogen at conditions effective to produce the 1,4-disubstituted cyclohexane compound of formula (I).

Suitable hydrogenation conditions include ambient temperature and a hydrogen pressure of 25 to 250 psi, 50 to 200 psi, or 50 to 100 psi.

The hydrogenation reaction time may be varied, depending on the reaction conditions chosen and the desired yield. Generally, the reaction time may vary, such as from 0.5 hours to 24 hours, or from 5 hours to 22 hours.

The hydrogenation reaction may be carried out in the presence of a hydrogenation catalyst. Hydrogenation catalysts are typically based on Group VIII metals, such as platinum, palladium, nickel, or mixtures thereof. The metals can be present in pure form, as alloys, metal oxides, or mixtures thereof. The catalyst can be used in a homogeneous manner, but is generally used on a support. The support can be any solid material useful for heterogeneous catalysts. Examples of catalyst supports include aluminum oxides, spinels, zeolites, and carbon.

The catalyst can be used in an amount ranging from 0.01 to 15 mole percent, or from 0.1 to 10 mole percent, of catalytic metal, based on the amount of the cyclohexene compound (III).

The hydrogenation reaction may be carried out in the presence of an organic solvent. Suitable solvents include chlorinated hydrocarbons, acyclic ethers, cyclic ethers, alcohols such as methanol and ethanol, esters such as ethyl acetate, and aromatic hydrocarbons from the Diels-Alder reaction.

The cyclohexene compound (III) may be present in an amount ranging from 1 to 15 weight percent, or from 5 to 12 weight percent, based on total weight of the reaction mixture.

If "A" in formula (I) is an ester or a silyl ether group, the compound of formula (I) may be contacted with water at conditions effective to produce 1,4-cyclohexane-dimethanol. Suitable hydrolysis conditions include treating the compound of formula (I) with potassium carbonate or acetic acid in methanol at ambient temperature, or below (e.g., 0° C.), or treating the compound (I) with a soluble fluoride-containing reagent (such as $Bu_4NF$) under aprotic conditions.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations. These values and ranges may vary from their stated numbers depending upon the desired properties sought to be obtained by the present invention as well as the variations resulting from the standard deviation found in the measuring techniques. Moreover, the ranges described herein are intended and specifically contemplated to include all subranges and values within the stated ranges. For example, a range of 50 to 100 is intended to include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention.

EXAMPLES

GC Method

The components of interest that contain hydroxyl and carboxylic acid functionalities, including water, present in the samples were first quantitatively reacted with BSTFA (N,O-bis(trimethylsilyl)trifluoroacetamide) in the presence of pyridine to form the corresponding TMS-derivatives, which were then separated and quantified by an internal standard (ISTD) area % calibrated GC method.

The volume ratio of sample to derivatization reagent (BSTFA) and pyridine (containing the ISTD, decane) was 0.03 g:1 mL:0.2 mL in a GC vial, which was heated at 80° C. for 30 minutes to ensure complete derivatization.

Other components of interest without containing the reactive functionalities, such as esters and hydrocarbons, will remain intact during the BSTFA derivatization reaction.

The GC method used a DB-5 (or equivalent) capillary column (30 meters×0.32 mm ID×0.25 µm film thickness), a split injector (at 330° C.), a flame ionization detector (at 300° C.), helium carrier gas at a constant linear velocity of 20.4 cm/sec (by using a Shimadzu GC 2010 or equivalent) or at an initial column head pressure of 5.7 psi, an oven temperature program of 40° C. initial temp for 6 min, and 15° C./min temp ramp to 300° C. for 6.66 min final hold time.

1-µL of the prepared sample solution was injected with a split ratio of 40:1. The method provided quantification range of 0.01-100 area % for each component, such as terephthalic acid, cyclohexane-1,4-dicarboxlic acid, 1,4-cyclohexanedimethanol, dimethyl terephthalate, dimethyl cyclohexane-1,4-dicarboxylate and water.

Example 1

Preparation of (2E,4E)-hexa-2,4-diene-1,6-diol (2E,4E)-Hexa-2,4-diene-1,6-diol was prepared according to Equation

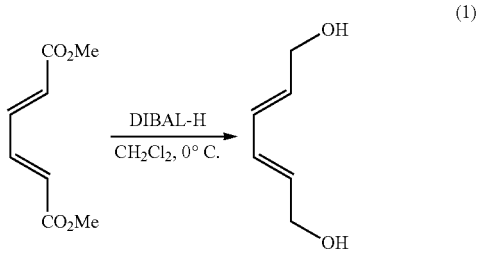 [SMILES: COC(=O)/C=C/C=C/C(=O)OC ; OC/C=C/C=C/CO]

trans,trans-Dimethyl muconate (7.00 g, 41.1 mmol) was dissolved in dichloromethane (0.50 M, 82 mL). The mixture was cooled to 0° C. Then DIBAL-H (di-isobutyl aluminum hydride) (25 weight percent solution in toluene, 98.0 g, 173 mmol) was cannulated directly from the reagent bottle over a 20-minute period. After 3.15 hours at 0° C., the excess DIBAL was quenched by the addition of ethyl acetate (50 mL). Then 100 mL of a saturated solution of NaK tartrate was carefully added (caution: significant exotherm upon quenching). The resulting mixture was diluted with 100 mL of ethyl acetate and allowed to stir overnight. The layers were separated. The aqueous phase was extracted twice with 200 mL of ethyl acetate. The organics were combined and dried with potassium carbonate. After filtration, the volatiles were removed under reduced pressure to reveal a white solid. After suspending in diethyl ether, the solid was filtered, collected, and used without further purification (3.51 g, 75% yield). $^1$H NMR δ (DMSO-$d_6$): 6.16 (m, 2H), 5.72 (m, 2H), 4.72 (at, J=6 Hz, 2H), 3.97 (at, J=3.0 Hz, 4H).

Example 2

Preparation of (3R,6S)-cyclohex-1-ene-1,4-dimethanol (3R,6S)-Cyclohex-1-ene-1,4-dimethanol was prepared according to Equation 2.

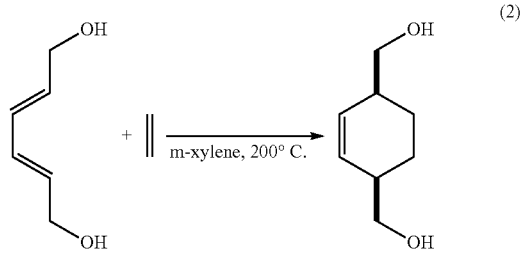

The diene diol (2.13 g, 18.7 mmol) was charged into a 300-mL autoclave. m-Xylene (75 mL, 0.25 M) was then added. The autoclave was sealed and pressure checked to 1200 psig with nitrogen. The autoclave was then purged with approximately 300 psig of nitrogen. The manifold was purged with ethylene two times. The autoclave was then purged with approximately 200 psig of ethylene. Stirring was initiated at 800 rpm. The autoclave was pressurized with 500 psig of ethylene. The pressure was maintained from the surge tank. The gas inlet valve was closed, and the autoclave was heated to 200° C. After reaching the desired temperature, the final pressure was 1,099 psig. The temperature was maintained for 12 hrs. After this time, the autoclave was cooled to ambient temperature, vented, and discharged. The volatiles were removed under reduced pressure to reveal the product as a pale yellow oil (0.67 g, 25% yield, 90% conversion). $^1$H NMR δ (CDCl$_3$): 5.77 (m, 2H), 3.57 (m, 4H), 2.32 (m, 2H), 1.77-1.57 (m, 4H).

Example 3

Preparation of (3R,6S)-cyclohex-1-ene-1,4-dimethanol using catechol (3R,6S)-Cyclohex-1-ene-1,4-dimethanol was prepared according to Equation 3.

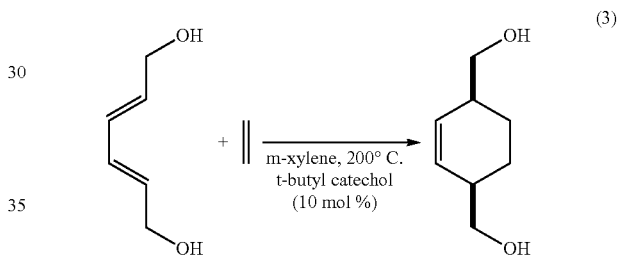

The diene diol (1.0 g, 8.76 mmol) was charged into a 300-mL autoclave. t-Butyl catechol (150 mg, 0.88 mmol) and m-xylene (70 mL, 0.125 M) were then added. The autoclave was sealed and pressure checked to 1200 psig with nitrogen. The autoclave was then purged with ~300 psig of nitrogen. The manifold was purged twice with ethylene. The autoclave was then purged with ~200 psig of ethylene. Stirring was initiated at 800 rpm. The autoclave was pressurized with 500 psig of ethylene. The pressure was maintained from the surge tank. The gas inlet valve was closed, and the autoclave was heated to 200° C. After reaching the desired temperature, the final pressure was 1,217 psig. The temperature was maintained for 12 hours. After this time, the autoclave was cooled to ambient temperature, vented, and discharged.

The crude reaction material contained black particulates. Enough ethyl acetate was added to dissolve all of the solids. GC-MS analysis of the crude mixture indicated only the cycloadduct as major product. The volatiles were then removed under reduced pressure. $^1$H NMR indicated a very clean conversion. The crude material was passed through a short plug of silica and washed with ethyl acetate. NMR still indicated catechol. The material was then chromatographed on silica gel (4:1 to 1:1 to 0:1 hexanes:ethyl acetate) to ultimately provide a colorless oil. The volatiles were removed under reduced pressure to reveal the product as a colorless oil (the unreacted diene starting material was not separated in the chromatography) (0.73 g, 58% yield, 87% conversion). $^1$H NMR δ (CDCl$_3$): 5.77 (m, 2H), 3.57 (m, 4H), 2.32 (m, 2H), 1.77-1.57 (m, 4H).

Example 4

Preparation of (3R,6S)-cyclohex-1-ene-3,6-dimethanol diacetate (3R,6S)-Cyclohex-1-ene-3,6-dimethanol diacetate was prepared according to Equation 4.

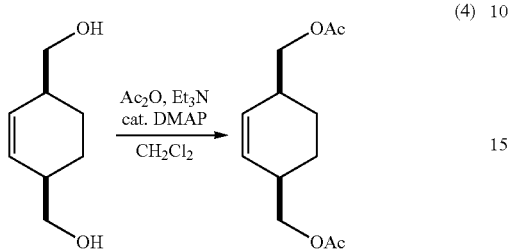

(4)

The ene diol product from Example 3 (0.73 g, 5.12 mmol) was dissolved in 10.2 mL of methylene chloride (0.50 M). Then triethylamine (1.78 mL, 12.8 mL) and DMAP (dimethylaminopyridine) (0.063 g, 0.51 mmol) were added. Acetic anhydride (1.09 mL, 11.5 mmol) was then added. After the exotherm subsided, the reaction was stirred for 1.75 hours at ambient temperature. After this time, 20 mL of water was added. The layers were separated. The aqueous layer was extracted with 5 mL of ethyl acetate. The organics were combined and dried with sodium sulfate. The organics were then passed through a short plug of silica gel, rinsing with ethyl acetate. The volatiles were removed under reduced pressure to reveal a colorless oil (1.14 g, 98% yield). $^1$H NMR δ (CDCl$_3$): 5.71 (m, 2H), 3.96 (d, J=6.0 Hz, 4H), 2.44 (m, 2H), 2.07 (s, 6H) 1.74-1.48 (m, 4H).

Example 5

Preparation of (1R,4S)-cyclohexane-1,4-dimethanol diacetate (1R,4S)-Cyclohexane-1,4-dimethanol diacetate was prepared according to Equation 5.

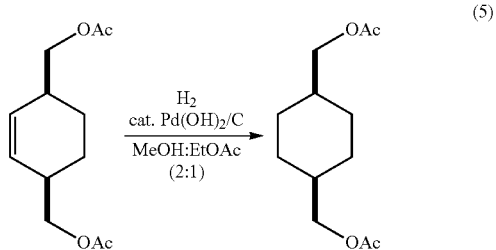 [SMILES: CC(=O)OC[C@@H]1C=C[C@H](COC(C)=O)CC1 ; "MeOH:EtOAc(2:1)" ; CC(=O)OC[C@H]1CC[C@@H](COC(C)=O)CC1]

(5)

The ene diacetate product from Example 4 (1.14 g, 5.04 mmol) was dissolved in a mixture of methanol:ethyl acetate (2:1, 50.4 mL, 0.10 M) and transferred to a Parr bottle. Pd(OH)$_2$/C (500 mg) was added. The bottle was placed into a Parr shaker. After purging with nitrogen, the bottle was pressurized to 50 psig with H$_2$. The bottle was shaken for 3.5 hours. After this time, the mixture was discharged from the bottle and filtered through a short plug of celite. The volatiles were removed under reduced pressure to reveal a pale yellow oil with a suspended white solid. The mixture was triturated with ether and filtered through a plug of cotton. After the volatiles were removed under reduced pressure, the material was used without further purification (1.08 g, 94% yield). $^1$H NMR δ (CDCl$_3$): 3.99 (d, J=6.0 Hz, 4H), 2.05 (s, 6H), 1.84 (m, 2H), 1.61-1.37 (m, 8H).

Example 6

Preparation of cis- and trans-cyclohexane-1,4-dimethanol cis- and trans-Cyclohexane-1,4-dimethanol were prepared according to Equation 6.

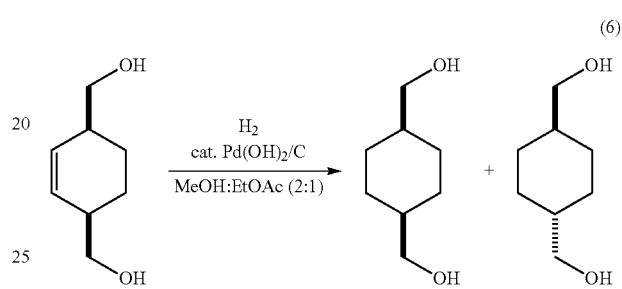

(6)

The ene diol (330 mg, 2.32 mmol) and Pd(OH)$_2$/C (120 mg) were charged into a 300-mL autoclave. A mixture of methanol:ethyl acetate (2:1, 34 mL, 0.068 M) was then added. The autoclave was sealed and then pressure checked to 1200 psig with nitrogen. The autoclave was purged with approx. 300 psig of nitrogen. The manifold was then purged twice with H$_2$. The autoclave was then purged with ~200 psig of H$_2$. Stirring was initiated at 800 rpm. The autoclave was pressurized with 200 psig of H$_2$. The pressure was maintained from the surge tank. After 6 hours at ambient temperature, the autoclave was vented and discharged. After filtration through a pad of celite, the volatiles were removed under reduced pressure to reveal the product as a colorless oil (178 mg recovered). GC analysis: 62.5% cis-CHDM, 21.7% trans-CHDM, and 15.8% unknown. $^1$H NMR δ (CDCl$_3$): 3.55 (bs, 4H), 2.07-0.86 (m, 10H).

Example 7

Preparation of cis- and trans-cyclohexane-1,4-dimethanol cis- and trans-Cyclohexane-1,4-dimethanol were prepared according to Equation 7.

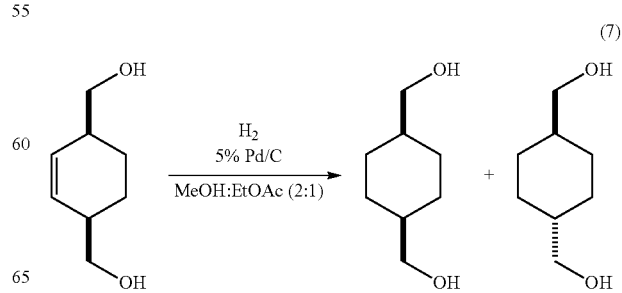

(7)

The ene diol (510 mg, 3.59 mmol) dissolved in a mixture of methanol:ethyl acetate (2:1, 36 mL, 0.10 M) was added to a Parr bottle. Then 5% Pd(OH)$_2$/C (500 mg) was added. The bottle was placed into a Parr shaker. After purging with nitrogen, the bottle was pressurized to 50 psig with of H$_2$. The bottle was shaken for 16 hours. After this time, the mix was discharged from the bottle and filtered through a short plug of celite. The volatiles were removed under reduced pressure to reveal a pale yellow oil (0.49 g recovered). GC analysis: 69.8% cis-CHDM, 16.6% trans-CHDM, 4.15% terephthalic acid (TPA), and 9.45% unknown. $^1$H NMR δ (CDCl$_3$): 3.55 (bs, 4H), 2.07-0.86 (m, 10H).

Example 8

Preparation of cis- and trans-cyclohexane-1,4-dimethanol

Cyclohexenedimethanol (510 mg, 3.59 mmol) dissolved in MeOH:EtOAc (2:1, 36 mL, 0.10 M) was added to a Parr bottle. Then 5% Pd/C (500 mg) was added. The bottle was placed into a Parr shaker. After purging with nitrogen, the bottle was pressurized to 50 psig with H$_2$. The bottle was shaken for 17.5 hours. After this time, the mixture was discharged from the bottle and filtered through a short plug of celite. The volatiles were removed under reduced pressure to reveal a pale yellow oil (0.48 g recovered). GC analysis: 73.3% cis-CHDM, 13.8% trans-CHDM, 4.55% terephthalic acid (TPA), and 8.35% unknown. $^1$H NMR δ (CDCl$_3$): 3.55 (bs, 4H), 2.07-0.86 (m, 10H).

Example 9

Preparation of cis- and trans-cyclohexane-1,4-dimethanol cis- and trans-Cyclohexane-1,4-dimethanol were prepared according to Equation 9.

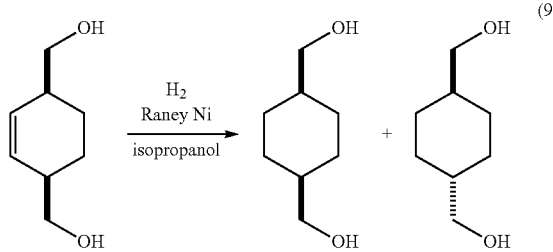

(9)

The ene diol (0.60 g, 4.22 mmol) dissolved in 42.2 mL of isopropanol (0.10 M) was added to a Parr bottle. Then 3.46 g of isopropanol-washed Raney Ni slurry was added. The bottle was placed into a Parr shaker. After purging with nitrogen, the bottle was pressurized to 50 psig with H$_2$. The bottle was shaken for 20 hrs. After this time, the mixture was discharged from the bottle and filtered through a short plug of celite with an methanol rinse. The volatiles were removed under reduced pressure to reveal a colorless oil (0.52 g recovered). GC analysis: 78.6% cis-CHDM, 15.1% trans-CHDM, 1.26% cyclohexane dicarboxylic acid (CHDA), and 5.04% unknown. $^1$H NMR δ (CDCl$_3$): 3.55 (bs, 4H), 2.07-0.86 (m, 10H).

Example 10

Preparation of (2E,4E)-hexa-2,4-diene-1,6-diacetate (2E,4E)-Hexa-2,4-diene-1,6-diacetate was prepared according to Equation 10.

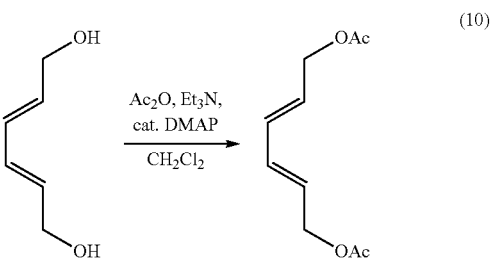 [SMILES: OC/C=C/C=C/CO ; "CH2Cl2" ; CC(=O)OC/C=C/C=C/COC(C)=O]

(10)

The diene diol (1.47 g, 12.9 mmol) was suspended in dichloromethane (0.50 M, 26 mL). Triethylamine (5.39 mL, 38.6 mmol) was added all at once followed by the addition of acetic anhydride (3.29 g, 32.2 mmol). Then a catalytic amount of DMAP (4-dimethylaminopyridine) (30 mg) was added. Upon addition of DMAP, the solution became homogeneous. The reaction was allowed to stir for 16 hours. The volatiles were then removed under reduced pressure. The crude mixture was loaded onto a column of silica gel and then subjected to flash column chromatography (4:1 hexanes:ethyl acetate). The product was isolated as a colorless oil (2.51 g, 98% yield). $^1$H NMR δ (CDCl$_3$): 6.28 (m, 2H), 5.80 (m, 2H), 4.60 (d, J=6.0 Hz, 4H), 2.08 (s, 6H).

Example 11

Preparation of (3R,6S)-cyclohex-1-ene-3,6-dimethanol diacetate (3R,6S)-Cyclohex-1-ene-3,6-dimethanol diacetate was prepared according to Equation 11.

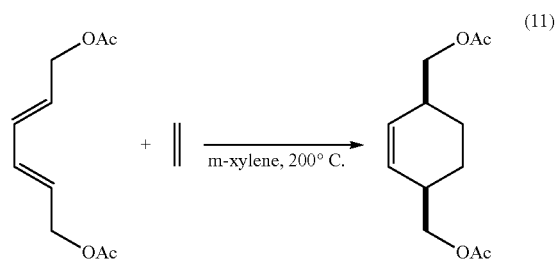

(11)

The diene diacetate (3.39 g, 17.1 mmol) was charged into a 300-mL autoclave. m-Xylene (102 mL, 0.25 M) was then added. The autoclave was sealed and then pressure checked to 1,200 psig with nitrogen. The autoclave was purged with ~300 psig of nitrogen. The manifold was then purged twice with ethylene. The autoclave was purged with ~200 psig of ethylene. Stirring was then initiated at 800 rpm. The autoclave was pressurized with 500 psig of ethylene. The pressure was maintained from the surge tank. The gas inlet valve was closed, and the autoclave was heated to 250° C. After reaching the desired temperature, the final pressure was 855 psig. The temperature was maintained for 6 hours. After this time, the autoclave was cooled to ambient temperature, vented, and discharged. The volatiles were removed under reduced pressure to reveal the product as a pale yellow oil. The mix was dissolved in diethyl ether (100 mL) and treated with carbon black. After filtration, the volatiles were stripped. $^1$H NMR analysis revealed a minor impurity. The mixture was chromatographed on silica gel using a heptane:EtOAc gradient (100:0 to 10:1 to 1:1). After the volatiles were stripped, the product was isolated as a pale yellow oil (3.29 g, 85% yield). $^1$H NMR δ (CDCl$_3$): 5.71 (m, 2H), 3.96 (d, J=6.0 Hz, 4H), 2.44 (m, 2H), 2.07 (s, 6H) 1.74-1.48 (m, 4H).

Example 12

Preparation of (3R,6S)-cyclohex-1-ene-3,6-dimethanol diacetate

The diene diacetate of Equation 11 (1.11 g, 5.60 mmol) was charged into a 100-mL autoclave. m-Xylene (11 mL, 0.50 M) was then added. The autoclave was sealed and then pressure checked to 1,500 psig with nitrogen. The autoclave was purged with ~300 psig nitrogen. The manifold was then purged twice with ethylene. The autoclave was purged with ~200 psig of ethylene. Stirring was then initiated at 800 rpm. The autoclave was pressurized with 500 psig of ethylene. The pressure was maintained from the surge tank. The gas inlet valve was closed, and the autoclave was heated to 250° C. After reaching the desired temperature, the final pressure was 1,195 psig. The temperature was maintained for 2 hrs. After this time, the autoclave was cooled to ambient temperature, vented, and discharged. The volatiles were removed under reduced pressure to reveal the product as a pale yellow oil (1.11 g recovered mass, 88% yield, quantitative conversion). $^1$H NMR δ (CDCl$_3$): 5.71 (m, 2H), 3.96 (d, J=6.0 Hz, 4H), 2.44 (m, 2H), 2.07 (s, 6H) 1.74-1.48 (m, 4H).

Example 13

Preparation of (3R,6S)-cyclohex-1-ene-3,6-dimethanol diacetate

The diene diacetate of Equation 11 (1.11 g, 5.60 mmol) was charged into a 100-mL autoclave. m-Xylene (11 mL, 0.50 M) was then added. The autoclave was sealed and then pressure checked to 1,500 psig with nitrogen. The autoclave was purged with ~300 psig of nitrogen. The manifold was then purged twice with ethylene. The autoclave was purged with ~200 psig of ethylene. Stirring was then initiated at 800 rpm. The autoclave was pressurized with 500 psig of ethylene. The pressure was maintained from the surge tank. The gas inlet valve was closed, and the autoclave was heated to 250° C. After reaching the desired temperature, the final pressure was 1,204 psig. The temperature was maintained for 1 hour. After this time, the autoclave was cooled to ambient temperature, vented, and discharged. The volatiles were removed under reduced pressure to reveal the product as a pale yellow oil (1.14 g, 90% yield, 95% conversion). $^1$H NMR δ (CDCl$_3$): 5.71 (m, 2H), 3.96 (d, J=6.0 Hz, 4H), 2.44 (m, 2H), 2.07 (s, 6H) 1.74-1.48 (m, 4H).

Example 14

Preparation of (3R,6S)-cyclohex-1-ene-3,6-dimethanol diacetate

The diene diacetate of Equation 11 (1.00 g, 5.05 mmol) was charged into a 100-mL autoclave. m-Xylene (10 mL, 0.50 M) was then added. The autoclave was sealed and then pressure checked to 1500 psig with nitrogen. The autoclave was purged with ~300 psig nitrogen. The manifold was then purged twice with ethylene. The autoclave was purged with ~200 psig of ethylene. Stirring was then initiated at 800 rpm. The autoclave was pressurized with 500 psig of ethylene. The pressure was maintained from the surge tank. The gas inlet valve was closed, and the autoclave was heated to 250° C. After reaching the desired temperature, the final pressure was 1,204 psig. The temperature was maintained for 10 minutes. After this time, the autoclave was cooled to ambient temperature, vented, and discharged. The volatiles were removed under reduced pressure to reveal the product as a pale yellow oil (1.04 g recovered mass, 85% conversion). $^1$H NMR δ (CDCl$_3$): 5.71 (m, 2H), 3.96 (d, J=6.0 Hz, 4H), 2.44 (m, 2H), 2.07 (s, 6H) 1.74-1.48 (m, 4H).

Example 15

Preparation of cis-cyclohexane-1,4-dimethanol diacetate cis-Cyclohexane-1,4-dimethanol diacetate was prepared according to Equation 15.

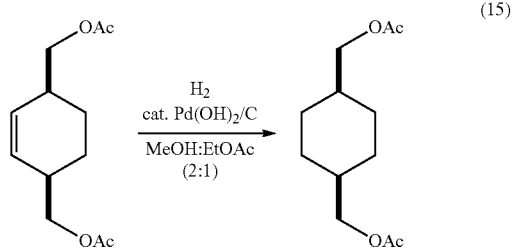 [SMILES: CC(=O)OC[C@@H]1C=C[C@H](COC(C)=O)CC1 ; CC(=O)OC[C@H]1CC[C@@H](COC(C)=O)CC1]

(15)

The ene diacetate (2.53 g, 11.2 mmol) was dissolved in a mixture of methanol:ethyl acetate (2:1, 112 mL, 0.10 M) and transferred to a Parr bottle. Pd(OH)$_2$/C (500 mg) was added. The bottle was placed into a Parr shaker. After purging with nitrogen, the bottle was pressurized to 50 psig with H$_2$. The bottle was shaken for 18 hours. After this time, the mixture was discharged from the bottle and filtered through a short plug of celite. The volatiles were removed under reduced pressure to reveal a pale yellow oil. The material was used without further purification (2.28 g, 89% yield). $^1$H NMR δ (CDCl$_3$): 3.99 (d, J=6.0 Hz, 4H), 2.05 (s, 6H), 1.84 (m, 2H), 1.61-1.37 (m, 8H).

Example 16

Preparation of cis-1,4-cyclohexanedimethanol by hydrolysis of its diacetate cis-1,4-Cyclohexanedimethanol was prepared according to Equation 16.

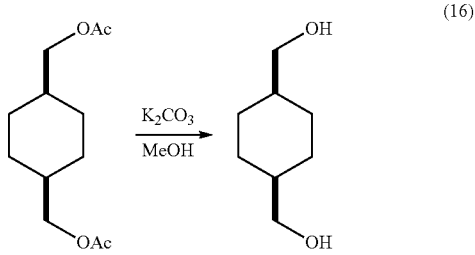

(16)

The diacetate (2.28 g, 9.99 mmol) was dissolved in 100 mL of methanol (0.10 M). Potassium carbonate (3.04 g, 21.9 mmol) was added all at once. The mixture was stirred for 17 hours at ambient temperature. The volatiles were then removed under reduced pressure. Water (100 mL) was added to the crude mix. The aqueous phase was then extracted three times with 100 mL of ethyl acetate. The organic extracts were combined and dried with $Na_2SO_4$. After filtration, the volatiles were removed under reduced pressure to yield a colorless oil (1.02 g recovered). GC analysis: 82.3% cis-CHDM, 0.44% trans-CHDM, and 17.3% unknown. $^1$H NMR δ ($CDCl_3$): 3.57 (d, J=6.0 Hz, 4H), 1.71 (m, 2H), 1.61-1.29 (m, 8H).

Example 17

Preparation of cis-1,4-cyclohexanedimethanol by hydrolysis of its diacetate

The diacetate product from Example 5 (1.08 g, 4.73 mmol) was dissolved in methanol (9.50 mL, 0.50 M). Potassium carbonate (1.44 g, 10.4 mmol) was added all at once. The mixture was stirred for 17 hours at ambient temperature. The volatiles were then removed under reduced pressure. Water (10 mL) was added to the crude mixture. The aqueous phase was extracted three times with 25 mL of ethyl acetate. The organic extracts were combined and dried with sodium sulfate. After filtration, the volatiles were removed under reduced pressure to yield a colorless oil (0.43 g recovered). GC analysis: 90.5% cis-CHDM, 0.48% trans-CHDM, 0.12% terephthalic acid (TPA), and 8.9% unknown. $^1$H NMR δ ($CDCl_3$): 3.57 (d, J=6.0 Hz, 4H), 1.71 (m, 2H), 1.61-1.29 (m, 8H).

Example 18

Preparation of 1,6-di-trimethylsiloxy-(2E,4E)-hexa-2,4-diene 1,6-Di-trimethylsiloxy-(2E,4E)-hexa-2,4-diene was prepared according Equation 18.

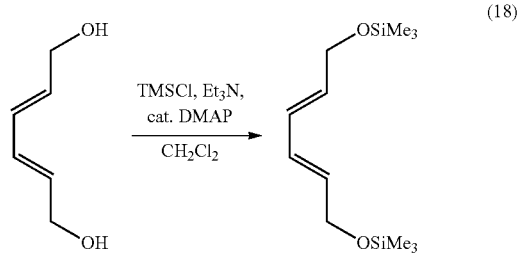

(18)

The diene diol (1.0 g, 8.76 mmol) was suspended in 17.5 mL of methylene chloride (0.50 mL). Then triethylamine (3.05 mL, 21.9 mmol) was added. Trimethylsilylchloride (TMSCl) (2.47 mL, 19.3 mmol) was added, followed by DMAP (10.7 mg, 0.088 mmol). The reaction was stirred for six hours at ambient temperature. The mixture was diluted and quenched with 100 mL of water. The layers were separated. The aqueous component was extracted with ethyl acetate. The organics were combined and dried with sodium sulfate. After filtration, the volatiles were removed under reduced pressure. The crude mixture was then triturated with ether and filtered through a short plug of silica. The volatiles were removed to reveal a colorless oil that was used without further purification (2.08 g, 92% yield). $^1$H NMR δ ($CDCl_3$): 6.21 (m, 2H), 5.75 (m, 2H), 4.18 (d, J=6.0 Hz, 4H), 0.13 (s, 6H).

Example 19

Preparation of (3R,6S)-3,6-bis(((trimethylsilyl)oxy) methyl) cyclohex-1-ene (3R,6S)-3,6-Bis(((trimethylsilyl)oxy)methyl) cyclohex-1-ene was prepared according to Equation 19.

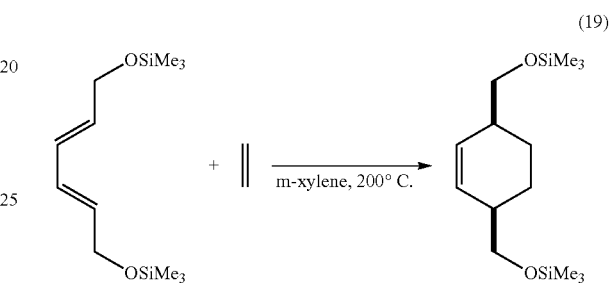

(19)

The diene disiloxy (2.08 g, 8.05 mmol) was charged into a 300 mL autoclave. m-Xylene (64 mL, 0.125 M) was then added. The autoclave was sealed and then pressure checked to 1,200 psig with nitrogen. The autoclave was purged with ~300 psig of nitrogen. The manifold was then purged twice with ethylene. The autoclave was then purged twice with ~200 psig ethylene. Stirring was initiated at 800 rpm. The autoclave was pressurized with 500 psig of ethylene. The pressure was maintained from the surge tank. The gas inlet valve was closed, and the autoclave was heated to 200° C. After reaching the desired temperature, the final pressure was 1,306 psig. The temperature was maintained for 12 hours. After this time, the autoclave was cooled to ambient temperature, vented, and discharged. The volatiles were removed under reduced pressure to reveal the product as a pale yellow oil (2.14 g recovered, 86% conversion). $^1$H NMR δ ($CDCl_3$): 5.68 (bs, 2H), 3.49-3.37 (m, 4H), 2.26 (m, 2H), 1.69-1.43 (m, 4H). 0.12 (s, 6H).

Example 20

Hydrogenation of (3R,6S)-3,6-bis(((trimethylsilyl) oxy)methyl) cyclohex-1-ene

The bis-trimethylsilylether derivative from Example 19 (2.14 g, 7.47 mmol) dissolved in a mixture of methanol:ethyl acetate (2:1, 74.7 mL, 0.10 M) was added to a Parr bottle. Then 5% $Pd(OH)_2$/C (1.00 g) was added. The bottle was placed into a Parr shaker. After purging with $N_2$, the bottle was pressurized to 50 psig with of $H_2$. The bottle was shaken for 11.5 hours. After this time, the mixture was discharged from the bottle and filtered through a short plug of celite. The volatiles were removed under reduced pressure to reveal a pale yellow oil (1.04 g recovered). GC analysis: 73.0% cis-CHDM, 8.92% trans-CHDM, and 18.1% unknown. $^1$H NMR δ ($CDCl_3$): 3.55 (bs, 4H), 2.07-0.86 (m, 10H).

Example 21

Preparation of (2E,4E)-hexa-2,4-diene-1,6-bis(t-butyldimethylsilylether)

(2E,4E)-Hexa-2,4-diene-1,6-bis(t-butyldimethylsilylether) was prepared according to Equation 21.

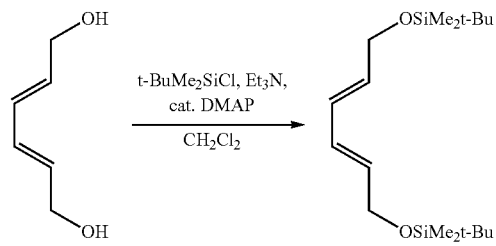

(21)

The diene diol (0.42 g, 3.68 mmol) was suspended in methylene chloride (7.4 mL, 0.50 mL). Then triethylamine (1.28 mL, 9.2 mmol) was added. t-Butyl-dimethyl-silylchloride (TBSCl) (1.22 g, 8.1 mmol) was added, followed by DMAP (45 mg, 0.37 mmol). The reaction was stirred for 30 minutes at ambient temperature. The mixture was diluted with additional methylene chloride and quenched with water. The layers were separated. The aqueous component was extracted with additional methylene chloride. The organics were combined and dried with sodium sulfate. After filtration, the volatiles were removed under reduced pressure. The crude mix was azeotroped with toluene to remove excess TBSOH. The crude mix was then triturated with ether and filtered through a short plug of silica. The volatiles were removed to reveal a white crystalline solid, which was used without further purification (1.02 g, 81% yield). $^1$H NMR δ (CDCl$_3$): 6.22 (m, 2H), 5.73 (m, 2H), 4.21 (d, J=6.0 Hz, 4H), 0.91 (s, 9H), 0.07 (s, 6H).

Example 22

Preparation of (3R,6S)-3,6-bis(((tert-butyldimethylsilyl)oxy)methyl) cyclohex-1-ene (3R,6S)-3,6-Bis(((tert-butyldimethylsilyl)oxy)methyl) cyclohex-1-ene was prepared according to Equation 22.

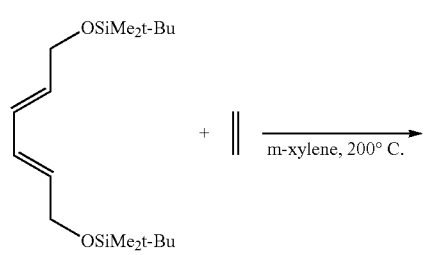

(22)

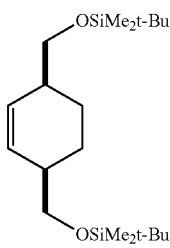

The diene disilyl ether (1.02 g, 2.98 mmol) was charged into a 300-mL autoclave. m-Xylene (24 mL, 0.25 M) was then added. The autoclave was sealed and then pressure checked to 500 psig with nitrogen. The autoclave was purged with ~300 psig of nitrogen. The manifold was then purged twice with ethylene. The autoclave was then purged with ~200 psig of ethylene. Stirring was initiated at 800 rpm. The autoclave was pressurized with 500 psig of ethylene. The pressure was maintained from the surge tank. The autoclave was held at ambient temperature and gas uptake was monitored until the autoclave was saturated with ethylene (held for 45 minutes). The gas inlet valve was closed and the autoclave was heated to 200° C. After reaching the desired temperature, the final pressure was 1,144 psig. The temperature was maintained for 12 hours. After this time, the autoclave was cooled to ambient temperature, vented, and discharged. The volatiles were removed under reduced pressure to reveal the product as a pale yellow oil (1.01 g recovered, 89% conversion). $^1$H NMR δ (CDCl$_3$): 5.68 (m, 2H), 3.46 (d, 4H), 2.25 (m, 2H), 1.67-1.45 (m, 4H), 0.90 (s, 9H), 0.05 (s, 6H).

To summarize the foregoing examples, highly efficient Diels-Alder reactions, which upon mild hydrogenation, can produce CHDM (or CHDM derivatives such as esters or silyl ethers, which can be readily hydrolyzed to yield CHDM). The Diels-Alder reactions proceeded with high retention of stereochemistry—yielding cis-isomers of CHDM or CHDM derivatives.

For instance, α,ω-difunctional hexadienes (see Equation 23 and Table 1 below) reacted with ethylene to yield corresponding cyclohexene derivatives. The conditions used for the reactions reported in Table 1 were designed to survey these dienes; they were not optimized. It is notable that a range of oxygen-containing functionality was tolerated (alcohol, ester, and ether). These dienes would be classified as "normal electron-demand" dienes in which the 1,4-dialkyl substitution of the diene group is "electron-rich," and an "electron-poor" dienophile would be expected to increase reaction rates. The reactivity of ethylene at these conditions was adequate to achieve high yielding reactions.

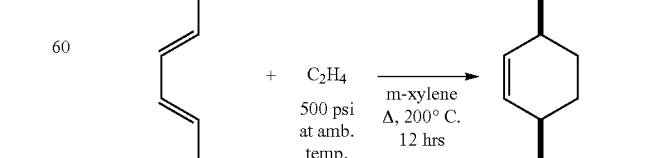

(23)

TABLE 1

Diels-Alder reactions of α,ω-difunctional hexadienes

| Example No. | Substituent A | Percent Yield of Dimethylcyclohexene Derivative |
|---|---|---|
| 2 | OH | 58 |
| 11 | OAc | 85 |
| 19 | OSiMe$_3$ | 86* |
| 22 | OSiMe$_2$(t-butyl) | 89* |

*The yields tabulated for Examples 19 and 22 are based $^1$H NMR analysis, not isolated yields.

It is well established that Diels-Alder reactions are stereospecific, and the trans,trans-hexadiene derivatives yield cis-disubstituted cyclohexenes. Only cis products were observed in the cycloadditions reported in Table 1.

Further insight into the reactivity of ethylene was gained from a study of the diene-diacetate cycloaddition (Examples 12-14) at 250° C. with reaction times of 2 hours, 1 hour, and 10 minutes. These experiments revealed quantitative conversions at 2 hours, 95% at 1 hour, and 85% after 10 minutes. Thus, the reaction proceeded to completion in less than two hours with significant conversion in only ten minutes. Rather than the very long reaction times reported in the prior art, it was surprising to find that time-efficient and highly selective cycloadditions could be carried out at temperatures of only 250° C. with dienes containing multiple oxygen-containing functional groups.

In a second step, the dimethylcyclohexene derivatives may be hydrogenated to produce dimethylcyclohexane derivatives, dehydrogenated to produce dimethylbenzene derivatives, or disproportionated to produce both (as shown in Equation 24 below). Thus, in the case where A=OH, for instance, 3,6-(dihydroxymethyl)cyclohexene may be converted to 1,4-cyclohexanedimethanol (1,4-CHDM) or 1,4-benzenedimethanol (known as xylylene glycol or 1,4-XG) or a mixture of these.

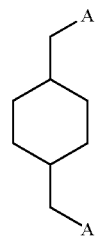

As summarized in Table 2, the hydrogenation reactions can occur under very mild conditions (ambient temperature, $P_{H2}$<100 psi) according to Equation 25 below.

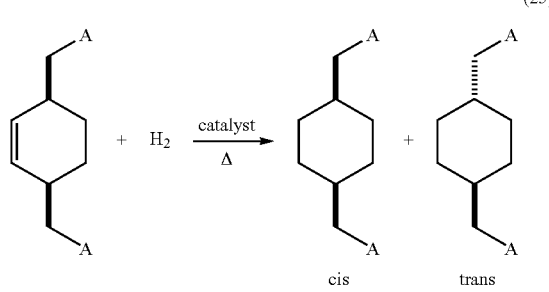

(25)

TABLE 2

Hydrogenation of 3,6-dimethylcyclohexene derivatives

| Example No. | Substituent A | Catalyst | Pressure (Psi) | Temp. (° C.) | Time (hr) | Cis/Trans Ratio | Percent Selectivity of Dimethyl-cyclohexane Derivative |
|---|---|---|---|---|---|---|---|
| 6 | OH | Pd(OH)$_2$ | 200 | 23 | 6.0 | 2.9 | 84 |
| 7 | OH | 5% Pd/C | 50 | 23 | 16.0 | 4.2 | 86 |
| 8 | OH | 5% Pd/C | 50 | 23 | 17.5 | 5.3 | 87 |
| 9 | OH | Ra-Ni | 50 | 23 | 20.0 | 5.2 | 94 |
| 15 | OAc | Pd(OH)$_2$/C | 50 | 23 | 18.0 | pure cis | 89 |
| 20 | OSiMe$_3$ | Pd(OH)$_2$/C | 50 | 23 | 11.5 | 8.2 | 82* |

*Hydrogenation and hydrolysis occurred simultaneously for the bis-silyl ether derivative yielding CHDM directly.

If the hydrogenation of the cyclohexene double bond occurs faster than its isomerization, then cis-dimethylcyclohexane derivative is produced. If isomerization produces the tri-substituted cyclohexene derivative shown in Equation 26 below, then ensuing hydrogenation yields a mixture of cis- and trans-dimethylcyclohexane derivatives.

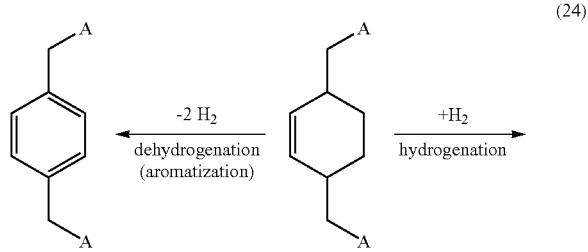

(24)

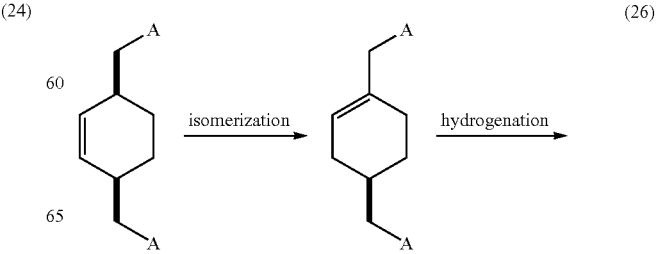

(26)

-continued

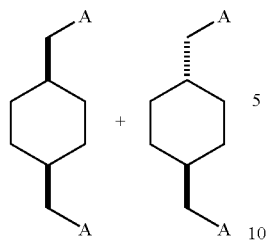

For the diacetate derivative (A=acetate), even with the Pd(OH)$_2$ catalyst which yields much isomerization for the diol derivative (A=OH), no isomerization of the cyclohexene was observed, and a pure cis-dimethylcyclohexane derivative was obtained. Hydrolysis of this diacetate (see Example 16) produced a very high cis (cis/trans=188) cyclohexanedimethanol. Such a product has not been directly produced by current technologies.

Polyesters and copolyesters made with CHDM are very sensitive to the cis:trans ratio of the CHDM employed. Polyester made from pure trans-CHDM and terephthalic acid has a T$_m$ of >310° C., while that made from pure cis-CHDM has a T$_m$>255° C. Access to very high cis content in such copolyesters has been limited by the commercial technologies for producing CHDM.

It is also possible to use isomerization to achieve a cis:trans ratio of 1:1. Thus, strategic use of isomerization to produce specific cis:trans ratios of commercial interest is possible for all ratios from a very high cis to equimolar (1:1) ratios. The ability to flex this ratio as a product of percent isomerization is an attractive feature of the two-step approach to CHDM synthesis described herein.

The invention has been described in detail with particular reference to preferred embodiments thereof, but it will be understood that variations and modifications can be effected within the spirit and scope of the invention.

We claim:

1. A process for preparing a 1,4-disubstituted cyclohexane compound of formula (I):

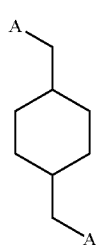
(I)

where A is —OH, —OR, Br, or Cl; and
R is a silyl group, a hydrocarbyl group, or an acyl group having 1 to 12 carbon atoms,
the process comprising:
(a) contacting ethylene with a (2E,4E)-hexa-2,4-diene compound of formula (II) at conditions effective to produce a 3,6-disubstituted cyclohex-1-ene compound of formula (III):

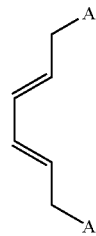
(II)

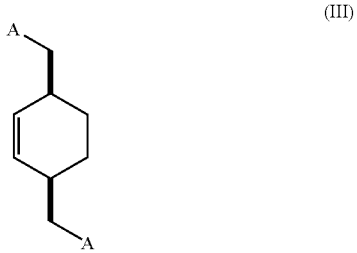
(III)

where A is as defined above; and
(b) contacting the 3,6-disubstituted cyclohex-1-ene compound of formula (III) with hydrogen at conditions effective to produce the 1,4-disubstituted cyclohexane compound of formula (I).

2. The process according to claim 1, wherein A is —OH.

3. The process according to claim 1, wherein A is Br, Cl, or —OR, and R is a silyl group or an acyl group.

4. The process according to claim 3, which further comprises:
(c) contacting the compound of formula (I) with water at conditions effective to produce 1,4-cyclohexandimethanol.

5. The process according to claim 1, wherein steps (a) or (b), or both, are carried out in a solvent.

6. The process according to claim 5, wherein the solvent comprises at least one of xylene, methanol, ethyl acetate, and methylene chloride.

7. The process according to claim 1, wherein step (a) is carried out in the absence of a catalyst.

8. The process according to claim 1, wherein step (a) is carried out in the presence of a catalyst.

9. The process according to claim 1, wherein the 1,4-disubstituted cyclohexane compound of formula (I) is produced in a cis:trans ratio of 1:1 to 1,000:1.

10. The process according to claim 1, wherein step (a) is carried out at a temperature of 140 to 300° C. and at 500 to 2,500 psig of ethylene.

11. The process according to claim 1, wherein step (b) is carried out at ambient temperature and at 25 to 250 psig of hydrogen.

12. The process according to claim 1, wherein step (b) is carried out in the presence of a hydrogenation catalyst comprising Pd or Ni.

* * * * *